US00PP37523P2

(12) United States Plant Patent
Hansen

(10) Patent No.: US PP37,523 P2
(45) Date of Patent: Jul. 14, 2026

(54) ***THALICTRUM* PLANT NAMED 'Cotton Candy'**

(50) Latin Name: ***Thalictrum* hybrid**
Varietal Denomination: Cotton Candy

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,870

(22) Filed: Oct. 14, 2025

(51) Int. Cl.
*A01H 6/72* (2018.01)
*A01H 5/02* (2018.01)

(52) U.S. Cl.
USPC ..... Plt./263.1

(58) Field of Classification Search
USPC ..... Plt./263.1
CPC ..... A01H 6/72; A01H 5/02
See application file for complete search history.

*Primary Examiner* — Keith O. Robinson

(57) ABSTRACT

The new and distinct cultivar of ornamental Meadow Rue, *Thalictrum* plant named 'Cotton Candy' with bipinnately to tripinnately compound foliage of medium green, wispy lavender-colored flowers on dark stems in late spring that appear well above the foliage. The new plant is winter-hardy and useful in the landscape.

2 Drawing Sheets

Latin botanical classification: *Thalictrum* hybrid.
Variety denomination: 'Cotton Candy'.

STATEMENT REGARDING PRIOR DISCLOSURES UNDER 37 CFR 1.77(B)(6)

The first offer for sale was made by Walters Gardens, Inc. on Oct. 23, 2023, to Edwards Greenhouse and Flowershop. On Dec. 1, 2023, the new plant was first advertised on a website managed by Walters Gardens, Inc. The plant was also listed in the "Walters Gardens 2024-2025 Catalog" published and released on May 23, 2024. Walters Gardens, Inc. obtained the new plant and all information about the new plant directly from the inventor. No plants of *Thalictrum* 'Cotton Candy' have been sold in this country or anywhere in the world, nor has any disclosure of the new plant been made more than one year prior the filing date of this application and such sale or disclosure within one year was either derived directly or indirectly from the inventor and therefore a 35 U.S.C. § 102(b) exception.

BACKGROUND OF THE INVENTION

The present invention relates to the new and distinct cultivar of Meadow Rue, botanically known as *Thalictrum* 'Cotton Candy', and hereinafter referred to as the cultivar 'Cotton Candy' or the "new plant." The new plant was an intentional cross by the inventor at a wholesale perennial nursery in Zeeland, Michigan, USA on Jun. 21, 2019, between *T. aquilegiifolium* 'Nimbus White' (not patented) as the female or seed parent and the male or pollen parent is a selection of *T. polygamum* known only as 'A' (not patented). The seeds were harvested on Aug. 7, 2019, and the new plant was assigned the breeder code 19-1-1 later in the evaluation process at the same nursery.

*Thalictrum* 'Cotton Candy' has been asexually propagated first in 2020 at the same nursery in Zeeland, MI by sterile plant tissue culture. Plants of 'Cotton Candy' have been found to be stable and identical to the original selection in multiple generations of asexual propagation.

SUMMARY OF THE INVENTION

The following traits have been repeatedly observed and represent the characteristics of the new cultivar. These attributes in combination distinguish 'Cotton Candy' as a unique cultivar of *Thalictrum:*

1. Tripinnately to bipinnately compound foliage of medium green;
2. Wispy lavender-colored flowers well above the foliage;
3. Winter-hardy habit with dark stems.

The female parent differs in having a shorter habit, white flowers and foliage that is bluish-green in color. The male parent differs in having a taller habit and white flowers.

The nearest comparison cultivars known to the inventor are: 'Nimbus Pink' (not patented), 'Black Stockings' (not patented), and 'Ghent Ebony' U.S. Plant Pat. No. 31,920.

*Thalictrum* 'Nimbus Pink' (not patented) has a much shorter habit and the flowers are lighter pinkish. 'Black Stockings' (not patented) has a taller habit with stems that are darker purple, and the flowers are a deeper purple. 'Ghent Ebony' has a more compact habit, darker grey-purple foliage, and white flowers.

BRIEF DESCRIPTION OF THE DRAWINGS

The photographs of the new plant demonstrate the unique traits and the overall appearance of *Thalictrum* 'Cotton Candy'. The colors are as accurate as reasonably possible with color reproductions. Variation in ambient light spectrum, source and direction may cause the appearance of minor variation in color. The plant used in the photographs was a two-year-old plant and was grown in a full-sun nursery trial garden in Zeeland, Michigan with supplemental water and fertilizer when needed. No pinching or plant growth regulators have been used.

DETAILED BOTANICAL DESCRIPTION

Figure 1:
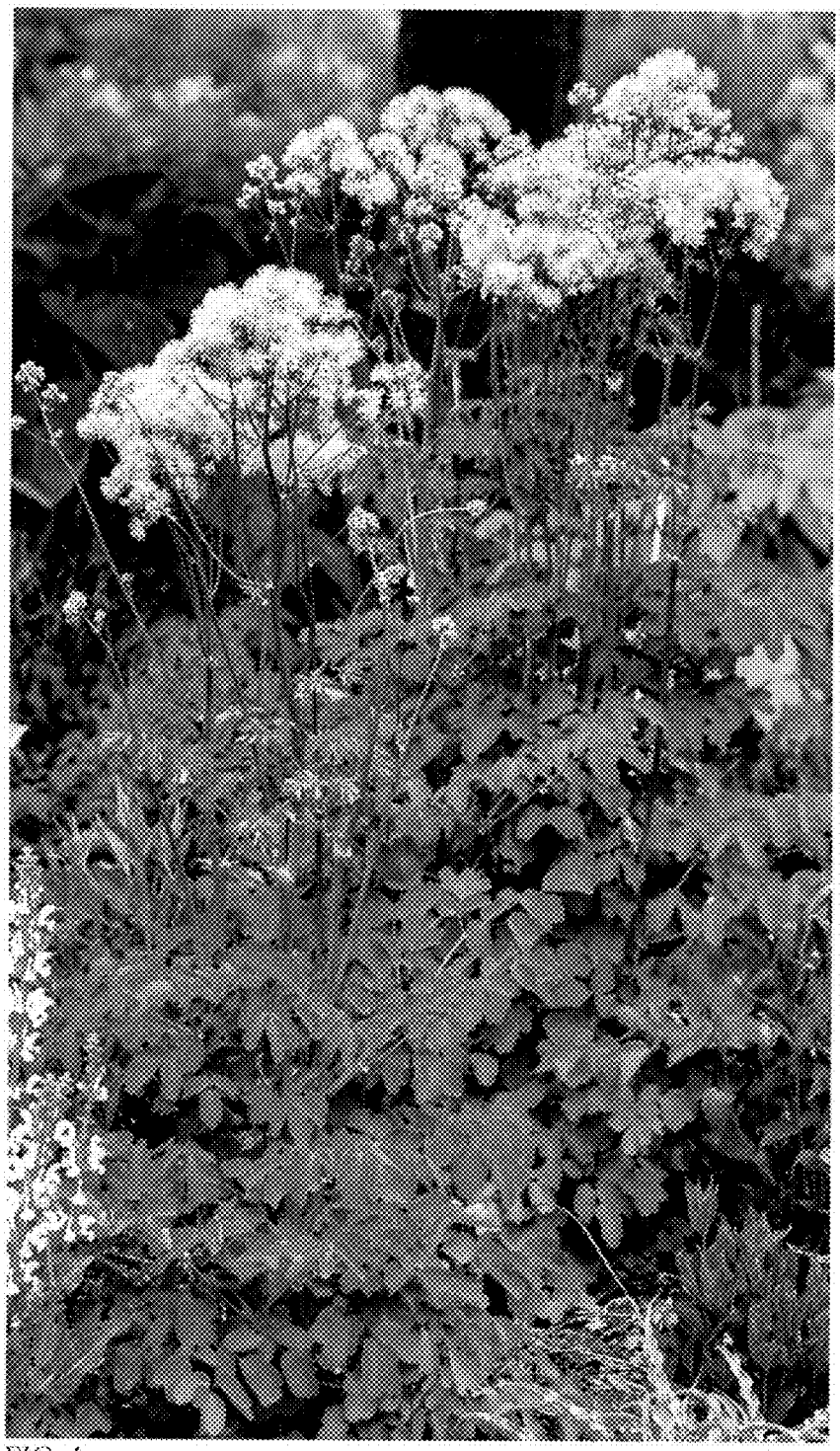
FIG. 1 shows the new plant in mid-season flowering habit.
Figure 2:
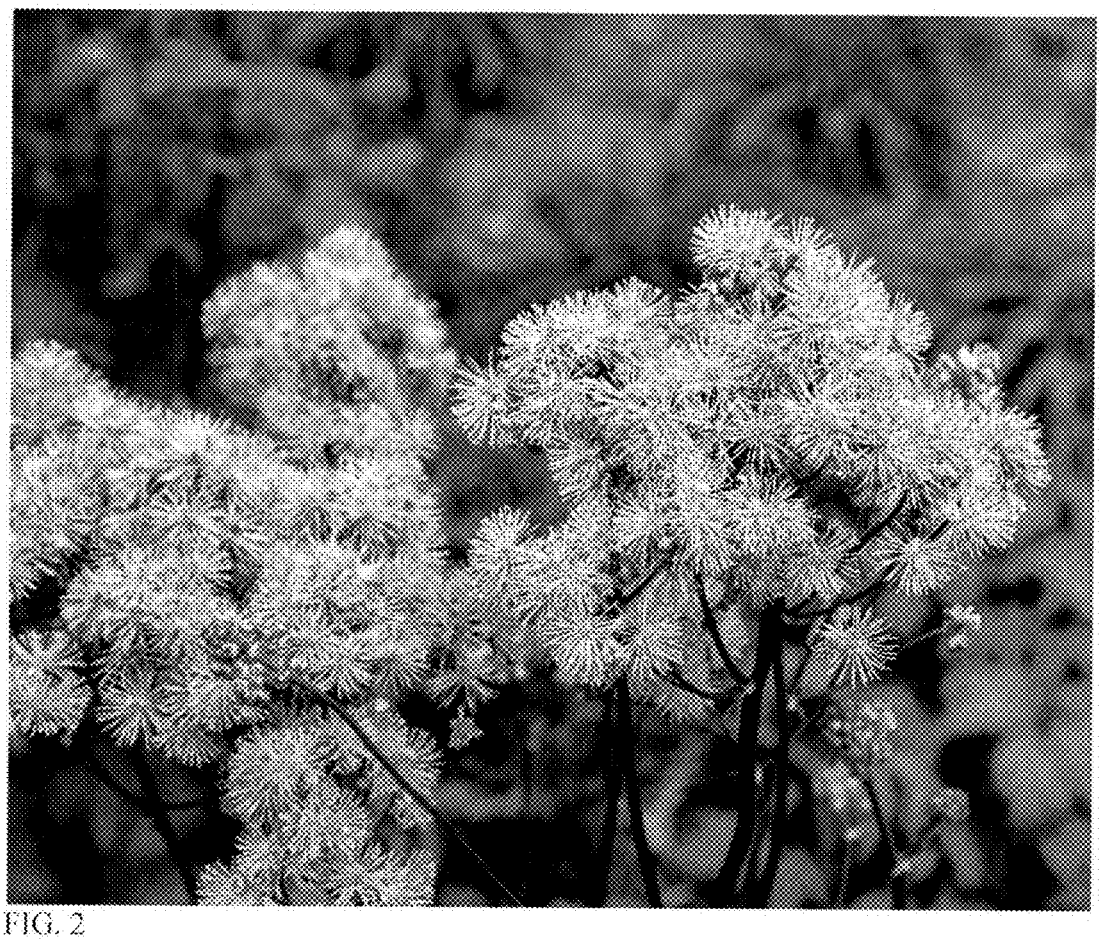
FIG. 2 shows a close-up of the flowers and buds.

The following descriptions and color references are based on the 2015 edition of The Royal Horticultural Society Colour Chart except where common dictionary terms are used. *Thalictrum* 'Cotton Candy' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in a full-sun trial garden in Zeeland, MI. Plants were given supplemental water and fertilizer but no plant growth regulators were used.

Botanical classification: *Thalictrum* hybrid;

Parentage: Female or seed parent is *Thalictrum aquilegiifolium* 'Nimbus White'; male or pollen parent is *T. polygamum* 'A';

Plant habit: Winter-hardy herbaceous perennial with mounded foliage and about 18 upright flowering stems extending well above the plant; foliage to about 75 cm wide and 90 cm tall, flowering scapes to about 118 cm tall;

Growth rate: Moderately vigorous, finishing in a 3.8-liter container in about 15 weeks;

Root: Fibrous; developing to about 2 mm diameter; heavily branched; color between RHS 165D and RHS N167D;

Stem: About 18 per plant; terete; fistulous; glabrous; slightly glaucous; lightly ribbed longitudinally; strength moderate; branching from base; to about 118 cm tall and 10 mm diameter;

Stem color: Proximally between RHS 144A and RHS 144B, distally nearest RHS 147B with strong blush to solid RHS 187A;

Nodes: 4 below inflorescence; average internode about 19.5 cm;

Node color: Proximally between RHS 144A and RHS 144B, distally nearest RHS 147B with strong blush to solid RHS 187A;

Foliage: Alternate; tripinnately compound; petiolate; broadly ovate to deltoid; basal foliage size up to 24 cm long and 35 cm wide; cauline foliage to 19 cm long and 15.5 cm wide;

*Leaflet*.—Typically 3 to 7; obovate; broadly acute apex; base cordate; adaxial and abaxial surfaces glabrous, smooth, and matte; with 3 shallowly dissected broadly acute lobes and 3 variably dissected lobes, shallowly dissected lobes dissected about 1 to 2 mm deep forming lobes to about 4 mm long and 6 mm wide; variably dissected lobes dissected 3 to 15 mm deep rarely to petiolule, forming lobes to 20 mm long and 12 mm wide; margins of leaflet entire; to about 35 mm long and 35 mm wide.

*Leaflet color*.—Young emerging nearest 138A adaxial and RHS 138B abaxial, maturing to between RHS 137A and RHS 137B with abaxial between RHS N138C and RHS 147C.

*Leaflet fragrance*.—None detected.

*Venation*.—Palmate; color adaxial nearest RHS 146B and abaxial nearest RHS 147C.

*Petiolules*.—Concavo-convex to applanate adaxial; glabrous; slightly lustrous; to about 12 mm long and 0.5 mm across; color adaxial proximal potion nearest RHS 200A, distal portion RHS 146A; abaxial nearest RHS 147B.

*Rachis*.—Terete; fistulous; glabrous; slightly lustrous; to about 23 cm long and 5 mm diameter at base above stipules; color adaxial nearest RHS 79A, abaxial where protected from higher light exposure nearest RHS 146D.

*Petioles*.—Terete; fistulous; clasping base; glabrous; slightly lustrous; to about 9 cm long and 4 mm diameter at base.

*Petioles and petiolules color*.—Nearest RHS 144B.

*Stipules*.—At each node of stem and rachis; base fused to be clasping or perfoliate; adaxial and abaxial glabrous and matte; on stem to about 20 mm long and 18 mm across near middle, on rachis to about 10 mm long and 8 mm across, decreasing distally; color between RHS 144B and RHS 144A both adaxial and abaxial.

Inflorescence: Terminal compound corymb; flowering to about 24 cm across and 15 cm tall;

Flower buds: Globose to obpyriform; glabrous, matte; about 5 mm diameter and 4 mm tall; color variable, nearest RHS N82A and RHS NN155D;

Flower: Actinomorphic; semi-globose; to about 2.5 cm across and 1.8 cm tall;

Flower fragrance: Faintly sweet;

Blooming period: Late spring for about 4 weeks;

Lastingness of individual flower: About 7 days;

Flower quantity: About 250 to 600 per stem;

Flower aspect: Outwardly to upwardly;

Calyx: Cruciform;

Tepals: Four; elliptic; obovate; concave; acute apex; cuneate base; entire margin; 6 mm long and 2 mm wide;

Tepal color: Variable, adaxial nearest RHS N82B and nearest RHS NN155D, abaxial nearest RHS N82B and nearest RHS NN155D;

Peduncle: Terete; fistulous; glabrous; slightly glaucous; strong; stiff; about 28 cm long from lowest branch and 5 mm diameter; aspect upright; branches at about 45° angle above horizontal; branches to about 24 cm long and 3 mm diameter;

Peduncle color: Nearest RHS 147B with strong blush to solid RHS 187A;

Pedicel: Cylindrical; glabrous; smooth; lustrous; to about 20 mm long and 0.7 mm diameter, average about 15 mm long and 0.7 mm in diameter; moderate in strength; aspect upwardly to outwardly;

Pedicel color: Nearest 146B;

Gynoecium: About 8 pistils; superior; on stipe;

*Stipe*.—To about 2 mm long and 0.2 mm diameter; aspect upright; color nearest RHS N77B.

*Stigma*.—Club-shaped, 0.5 mm long and 0.3 mm across; color nearest RHS 11D.

*Style*.—Cylindrical; short to about 0.2 mm long; color nearest RHS N77B.

*Ovary*.—Ellipsoidal with apex and base acute; glabrous; about 1 mm long and 0.5 mm across; color nearest RHS N77B.

Androecium: About 60 stamens;

*Filaments*.—Cylindrical; lustrous; about 14 mm long and 0.5 mm near apex; color nearest RHS 76A.

*Anthers*.—Oblong; to about 1 mm long and 0.5 mm in across; color nearest RHS N170D.

*Pollen*.—Low quantity; color nearest 11D.

Fruit and seed: Not yet been observed;

Pest and disease resistance: 'Cotton Candy' is resistant to *Odocoileus virginianus* and *Sylvilagus browsing*. Pest and disease resistance beyond what is typical of that of other Meadow Rue has not been observed.

Growth: The new plant is winter-hardy from USDA zones 5 to 8 and grows best with ample moisture, adequate drainage, and full sun.

I claim:

1. A new and distinct cultivar of *Thalictrum* plant named 'Cotton Candy' as herein described and illustrated.

* * * * *